United States Patent
Tadano

(10) Patent No.: US 11,890,062 B2
(45) Date of Patent: Feb. 6, 2024

(54) ESTIMATION DEVICE, ESTIMATION METHOD, AND PROGRAM

(71) Applicant: RIVERFIELD INC., Tokyo (JP)

(72) Inventor: Kotaro Tadano, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 857 days.

(21) Appl. No.: 16/967,058

(22) PCT Filed: Aug. 28, 2019

(86) PCT No.: PCT/JP2019/033810
§ 371 (c)(1),
(2) Date: Aug. 3, 2020

(87) PCT Pub. No.: WO2020/045538
PCT Pub. Date: Mar. 5, 2020

(65) Prior Publication Data
US 2021/0030484 A1  Feb. 4, 2021

(30) Foreign Application Priority Data
Aug. 30, 2018 (JP) .................. 2018-161363

(51) Int. Cl.
*A61B 34/20* (2016.01)
*A61B 34/30* (2016.01)
(Continued)

(52) U.S. Cl.
CPC .......... *A61B 34/20* (2016.02); *A61B 1/00149* (2013.01); *A61B 34/30* (2016.02);
(Continued)

(58) Field of Classification Search
CPC ..... A61B 34/20; A61B 1/00149; A61B 34/30; A61B 90/06; A61B 2034/2046; A61B 2034/301; A61B 2090/061
See application file for complete search history.

(56) References Cited

U.S. PATENT DOCUMENTS 5,762,458 A 6/1998 Wang et al.
10,716,458 B2 * 7/2020 Hayashi ............. A61B 1/00154
(Continued)

FOREIGN PATENT DOCUMENTS

JP 2000505328 A 5/2000
JP 2015524309 A 8/2015
(Continued)

OTHER PUBLICATIONS

International Preliminary Report on Patentability for International Patent Application No. PCT/JP2019/033810, dated Mar. 11, 2021, 13 pages including translation.
(Continued)

*Primary Examiner* — Kira Nguyen
(74) *Attorney, Agent, or Firm* — Withrow & Terranova, P.L.L.C.; Vincent K. Gustafson

(57) ABSTRACT

An estimation device calculates a first perpendicular vector and a second perpendicular vector. The first perpendicular vector is a component of a vector in a movement of a first position, which is a provisional pivot position of a surgical tool, the component being perpendicular to a direction of an axis of the surgical tool. The second perpendicular vector is a component of a vector in a movement of a second position of the surgical tool, the component being perpendicular to the direction of the axis. Then, a first distance, which is a length from a reference point on a rear end side or a reference point on a front end side of the surgical tool to the first position, is updated based on an inner product of the first and second perpendicular vectors.

7 Claims, 7 Drawing Sheets

(51) Int. Cl.
  *A61B 90/00* (2016.01)
  *A61B 1/00* (2006.01)
(52) U.S. Cl.
  CPC ...... *A61B 90/06* (2016.02); *A61B 2034/2046* (2016.02); *A61B 2034/301* (2016.02); *A61B 2090/061* (2016.02)

(56) References Cited

U.S. PATENT DOCUMENTS

| | | | |
|---|---|---|---|
| 11,534,241 B2* | 12/2022 | Kurihara | A61B 1/00009 |
| 2003/0083648 A1 | 5/2003 | Wang et al. | |
| 2007/0013336 A1 | 1/2007 | Nowlin et al. | |
| 2010/0016666 A1* | 1/2010 | Hasegawa | A61B 34/71 600/118 |
| 2013/0018255 A1* | 1/2013 | Kitamura | G06T 19/003 600/424 |
| 2014/0358161 A1* | 12/2014 | Hourtash | B25J 9/1607 901/15 |
| 2015/0202015 A1 | 7/2015 | Elhawary et al. | |
| 2019/0133704 A1* | 5/2019 | Hiratsuka | A61B 34/37 |

FOREIGN PATENT DOCUMENTS

| | | |
|---|---|---|
| JP | 2018088996 A | 6/2018 |
| WO | 2006124390 A2 | 11/2006 |

OTHER PUBLICATIONS

International Search Report (Form PCT/ISA/210) with English Translation for International Application No. PCT/JP2019/033810, dated Nov. 5, 2019, 4 pages including translation.

Written Opinion (Form PCT/ISA/237) with partial English Machine Translation for International Application No. PCT/JP2019/033810, dated Nov. 5, 2019, 6 pages including partial English machine language translation.

International Search Report (Form PCT/ISA/210) with English Translation for International Application No. PCT/JP2017/033810, dated Nov. 5, 2019, 4 pages including translation.

Written Opinion (Form PCT/ISA/237) with partial English Machine Translation for International Application No. PCT/JP2017/033810, dated Nov. 5, 2019, 6 pages including partial English machine language translation.

* cited by examiner

ESTIMATION DEVICE, ESTIMATION METHOD, AND PROGRAM

CROSS-REFERENCE TO RELATED APPLICATION

This application is the U.S. national phase under 35 U.S.C. § 371 of International Application No. PCT/JP2019/033810, which claims the benefit of Japanese Patent Application No. 2018-161363 filed on Aug. 30, 2018 with the Japan Patent Office, wherein the entire disclosures of the foregoing applications are hereby incorporated by reference herein.

TECHNICAL FIELD

The present disclosure relates to an estimation device, an estimation method, and a program that are related with a surgical assist robot used in endoscopic surgery and so forth.

BACKGROUND ART

Nowadays, endoscopic surgery using a surgical assist robot is becoming common. In the endoscopic surgery, a laparoscope, an endoscope, or forceps and others (hereinafter, also described as "surgical tools") attached to the surgical assist robot are used. It is proposed that these surgical assist robots be configured such that movements of the surgical tools are controlled based on a coordinate system that is set in the surgical assist robots (see Patent Document 1, for example).

PRIOR ART DOCUMENTS

Patent Documents

Patent Document 1: Japanese Unexamined Patent Application Publication No. 2018-088996

SUMMARY OF THE INVENTION

Problems to be Solved by the Invention

Patent Document 1 mentioned above discloses a technique for aligning a leading end of a surgical tool on a model of an internal organ of a subject's body. Specifically, a technique is proposed in which conversion formula converting actual coordinates of the leading end of the surgical tool into corresponding model coordinates is updated to a new conversion formula when the leading end of the surgical tool comes in contact with an inside wall of the internal organ.

However, the technique disclosed in Patent Document 1 may result in a decrease in alignment accuracy between a fixed point (hereinafter, also described as a "pivot position") of the surgical assist robot and an opening through which the surgical tool is inserted into the subject's body. In other words, this technique may result in the decrease in alignment accuracy between the pivot position of the surgical tool held by the surgical assist robot and an opening in a trocar, which is arranged on the subject's body as well as through which the surgical tool is inserted.

That is, the technique disclosed in Patent Document 1 enables estimation of a fixed position, namely a position of the leading end of the surgical tool; however, the pivot position of the surgical tool cannot be estimated. Further, the pivot position determined relatively with respect to the position of the end position of the surgical tool varies depending on a position or orientation of the surgical assist robot, the subject's body, or the surgical tool, for example. This also makes it difficult to estimate the pivot position based on the leading end position. Thus, the alignment accuracy between the pivot position of the endoscope and the opening in the trocar arranged on the subject's body may be decreased.

In one aspect of the present disclosure, it is desired that a pivot position of a surgical tool held by a surgical assist robot can be estimated.

Means for Solving the Problems

An estimation device of the present disclosure is configured to estimate a pivot position of a surgical tool, a rear end side of which being held by a holder of an arm, the arm including at least one joint. The estimation device comprises: a storage section configured to store a first distance, the first distance being: a length from a reference point on the rear end side of the surgical tool to a first position, which is a provisional pivot position, or a length from a reference point on a front end side of the surgical tool to the first position, the front end side being opposite to the rear end side; an obtainer configured to obtain: vector information, which is information on an orientation of the holder of the arm or on an orientation of the surgical tool, first information on a movement of the first position of the surgical tool, and second information on a movement of a second position of the surgical tool, the second positon being different from the first position; a vector calculator configured to calculate a direction of an axis of the surgical tool based on the vector information, and to individually calculate, based on the first information, the second information, and the direction of the axis of the surgical tool, a first perpendicular vector, which is a component of a vector in the movement of the first position, the component being perpendicular to the direction of the axis, and a second perpendicular vector, which is a component of a vector in the movement of the second position, the component being perpendicular to the direction of the axis; an inner product calculator configured to calculate an inner product of the first perpendicular vector and the second perpendicular vector; and an updater configured to update the first distance by adding a value of the inner product multiplied by a specified coefficient to the first distance stored in the storage section.

An estimation method of the present disclosure estimates a pivot position of a surgical tool, a rear end side of which being held by a holder of an arm, the arm including at least one joint. The estimation method comprises: obtaining vector information, which is information on an orientation of the holder of the arm or on an orientation of the surgical tool; obtaining first information on a movement of a first position, which is a provisional pivot position of the surgical tool, and second information on a movement of a second position of the surgical tool, the second positon being different from the first position; calculating a direction of an axis of the surgical tool based on the vector information obtained, and individually calculating, based on the first information, the second information, and the direction of the axis of the surgical tool, a first perpendicular vector, which is a component of a vector in the movement of the first position, the component being perpendicular to the direction of the axis, and a second perpendicular vector, which is a component of a vector in the movement of the second position, the component being perpendicular to the direction of the axis; updating a first distance, which is a length from a reference point on the rear end side of the surgical tool to the first position, or which is a length from a reference point on a front end side of the surgical tool to the first position, the front end side being opposite to the rear end side, by adding a value of the inner product multiplied by a specified coefficient to the first distance.

A program of the present disclosure estimates a pivot position of a surgical tool, a rear end side of which being held by a holder of an arm, the arm including at least one joint. The program causes a computer to execute functions comprising: obtaining vector information, which is information on an orientation of the holder of the arm or on an orientation of the surgical tool; obtaining first information on a movement of a first position, which is a provisional pivot position of the surgical tool, and second information on a movement of a second position of the surgical tool, the second positon being different from the first position; calculating a direction of an axis of the surgical tool based on the vector information obtained, and individually calculating, based on the first information, the second information, and the direction of the axis of the surgical tool, a first perpendicular vector, which is a component of a vector in the movement of the first position, the component being perpendicular to the direction of the axis, and a second perpendicular vector, which is a component of a vector in the movement of the second position, the component being perpendicular to the direction of the axis; updating a first distance, which is a length from a reference point on the rear end side of the surgical tool to the first position, or which is a length from a reference point on a front end side of the surgical tool to the first position, the front end side being opposite to the rear end side, by adding a value of the inner product multiplied by a specified coefficient to the first distance.

In these configurations, a calculation is made for the inner product of the component of the vector in the movement of the first position of the surgical tool (first perpendicular vector), the component being perpendicular to the direction of the axis of the surgical tool, and the component of the vector in the movement of the second position (second perpendicular vector), the component being perpendicular to the direction of the axis. Then, the first distance is updated on the basis of the inner product. This enables estimation of the pivot position of the surgical tool.

It is to be noted that the second position may be located in a rear end portion of the surgical tool.

The aforementioned configuration makes it easier to estimate the pivot position of the surgical tool.

Further, the vector information may comprise a rotation angle of the at least one joint measured by an angle sensor, and the vector calculator may calculate the direction of the axis of the surgical tool based on the rotation angle obtained from the angle sensor.

The aforementioned configuration makes it easier to obtain the vector information.

Further, the first information and the second information may comprise a rotation angle of the at least one joint measured after a specified time interval, and the vector calculator may calculate the first perpendicular vector and the second perpendicular vector based on the rotation angle of the at least one joint measured after the specified time interval.

The aforementioned configuration makes it easier to obtain the first information and the second information.

Further, the obtainer obtains the vector information, the first information, and the second information at specified sampling intervals, the vector calculator calculates the first perpendicular vector and the second perpendicular vector at the specified sampling intervals, the inner product calculator calculates a value of the inner product at the specified sampling intervals, and the updater updates the first distance at the specified sampling intervals.

Due to the aforementioned configuration, estimation accuracy of the pivot position of the surgical tool is increased. Further, if the pivot position of the surgical tool is moved due to some cause and the estimation accuracy of the pivot position is impaired, the first distance is repeatedly updated at the sampling intervals, thereby allowing a re-increase in the estimation accuracy of the pivot position of the surgical tool.

The aforementioned estimation device, estimation method, and program estimates the pivot position by updating the first distance based on the inner product of the first perpendicular vector and the second perpendicular vector. This allows estimation of the pivot position of the surgical tool held by the surgical assist robot.

EXPLANATION OF REFERENCE NUMERALS

10 . . . estimation device, 11 . . . obtainer, 12 . . . storage section, 13 . . . vector calculator, 14 . . . inner product calculator, 15 . . . updater, 50 . . . arm device (arm), 52 . . . rotating portion (joint), 52$s$ . . . rotation sensor (angle sensor), 55$p$, 56$p$ . . . pins (joints), 55$s$ . . . first link sensor (angle sensor), 56$s$ . . . second link sensor (angle sensor), 62 . . . first joint portion (joint), 63 . . . second joint portion (joint), 64 . . . third joint portion (joint), 62$s$ . . . first joint sensor (angle sensor), 63$s$ . . . second joint sensor (angle sensor), 64$s$ . . . third joint sensor (angle sensor), 70 . . . surgical tool, $P_p$ . . . pivot position, $P_p'$ . . . provisional pivot position, $\Delta P_p'$ . . . first movement vector, $\Delta P_r$ . . . second movement vector, $\Delta P_p \perp'$ . . . first perpendicular vector, $\Delta P_r \perp$ . . . second perpendicular vector, d' . . . first distance

MODE FOR CARRYING OUT THE INVENTION

Figure 1:
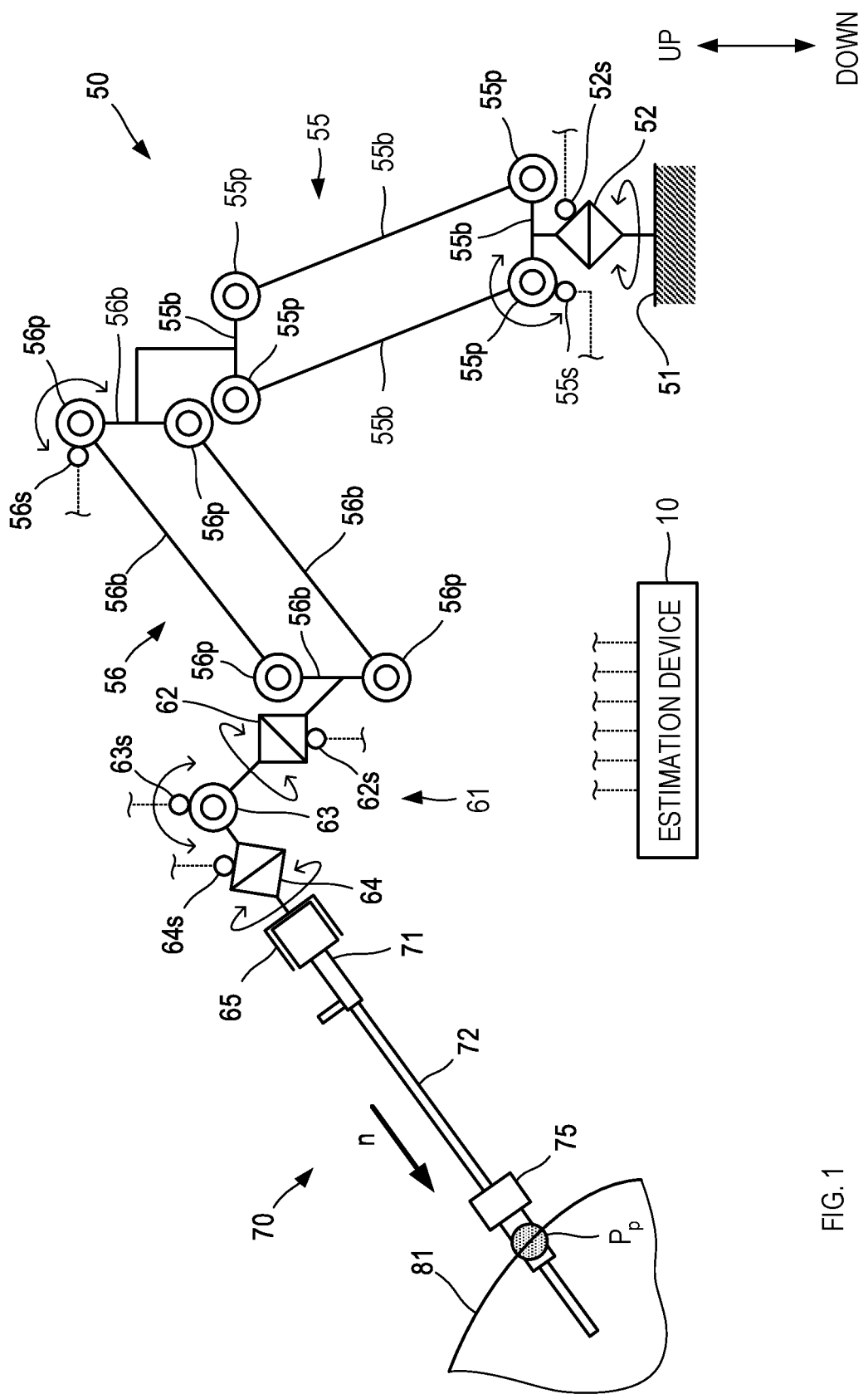
FIG. 1 is a schematic diagram of an estimation device and an arm device to which the estimation device is applied.

An estimation device 10 according to one embodiment of the present disclosure will be described below with reference to FIGS. 1 to 7. In the present embodiment, as one example, the estimation device 10 is used for an arm device (arm) 50 in a surgical assist robot or the like used in endoscopic surgery, as shown in FIG. 1.

The arm device 50 supports a surgical tool 70 such that a position and orientation of the surgical tool 70 can be changed. The arm device 50 is controlled such that the surgical tool 70 passes through a pivot position $P_p$, which is a specified relative position with respect to the arm device 50, if the position and/or orientation of the surgical tool 70 is changed. The pivot position $P_p$ substantially matches an arrangement position of a trocar 75 arranged at an abdominal wall 81 of a patient undergoing endoscopic surgery.

The surgical tool 70 may be various instruments, such as an endoscope or forceps, for use in endoscopic surgery. In the present embodiment, an endoscope is employed as one example of the surgical tool 70.

The surgical tool 70, namely the endoscope, mainly comprises a main body 71 and a tubular portion 72. The main body 71 is held by the arm device 50 and accommodates an imaging device converting an image, which is introduced through the tubular portion 72, into an electronic signal.

The tubular portion 72 has a tube or rod shape, and is inserted through the trocar 75, thus penetrating the abdominal wall 81 of the patient. Further, the tubular portion 72 is configured such that the image can be transmitted from its leading end to the main body 71.

As shown in FIG. 1, the arm device 50 mainly comprises a rotating portion (joint) 52, a first link portion 55, a second link portion 56, a gimbal portion 61, and a holder 65. The rotating portion 52, the first link portion 55, and the second link portion 56 are driven and controlled on the basis of a control signal input from a controller or the like (not shown) of the arm device 50.

The rotating portion 52 is a joint arranged in a part of the arm device 50 to be fixed to a base 51. The rotating portion 52 is configured to be capable of being driven and rotated around a rotation axis extending in an up-down direction, and is not limited to a specific configuration. The rotating portion 52 is provided with a rotation sensor (angle sensor) 52s detecting a rotation angle of the rotating portion 52.

The first link portion 55 is arranged between the rotating portion 52 and the second link portion 56, and is driven by an actuator (not shown). The first link portion 55 includes two pairs of bars 55b, each pair having the bars 55b in parallel, so as to be shaped like a rectangle with these bars 55b. The bar 55b and the bar 55b are coupled at an intersection thereof by a pin (joint) 55p allowing rotation of one degree of freedom.

Further, the first link portion 55 is provided with a first link sensor (angle sensor) 55s detecting a rotation angle of the specified pin 55p. In the present embodiment, as one example, the first link portion 55 extends in the up-down direction.

The second link portion 56 is arranged between the first link portion 55 and the gimbal portion 61, and is driven by an actuator (not shown). Similar to the first link portion 55, the second link portion 56 includes two pairs of bars 56b, each pair having the bars 56b in parallel, so as to be shaped like a rectangle with these bars 56b. The adjacent two bars 56b are coupled to each other by a pin (joint) 56p allowing rotation of one degree of freedom.

Further, the second link portion 56 is provided with a second link sensor (angle sensor) 56s detecting a rotation angle of the specified pin 56p. In the present embodiment, as one example, the second link portion 56 extends in a lateral direction (a direction along a plane intersecting the up-down direction).

The gimbal portion 61 is arranged between the second link portion 56 and the holder 65. The gimbal portion 61 comprises a first joint portion (joint) 62, a second joint portion (joint) 63, and a third joint portion (joint) 64, whose rotation axes intersect with each other. The gimbal portion 61 further comprises a first joint sensor (angle sensor) 62s detecting a rotation angle of the first joint portion 62, a second joint sensor (angle sensor) 63s detecting a rotation angle of the second joint portion 63, and a third joint sensor (angle sensor) 64s detecting a rotation angle of the third joint portion 64.

The first joint portion 62 is arranged adjacent to the second link portion 56. The first joint portion 62 is arranged such that the rotation axis thereof extends obliquely upward from a horizontal plane. More preferably, for example, the first joint portion 62 may be arranged such that the rotation axis thereof extends obliquely upward at an angle of 45 degrees with respect to the horizontal plane.

The second joint portion 63 is arranged between the first joint portion 62 and the third joint portion 64. The third joint portion 64 is arranged adjacent to the holder 65. The first to third joint portions 62 to 64 are not limited to specific configurations as long as they can rotate about the rotating axes thereof.

The holder 65 is arranged at a position adjacent to the gimbal portion 61, namely, at a front end of the arm device 50. The holder 65 is not limited to a specific configuration as long as it can hold the surgical tool 70.

The estimation device 10 estimates the pivot position $P_p$ of the surgical tool 70 held by the arm device 50. The pivot position $P_p$ is output to, for example, the controller or the like controlling the arm device 50. Further, the pivot position $P_p$ may be expressed as a position in a coordinate system used in the arm device 50.

Figure 2:
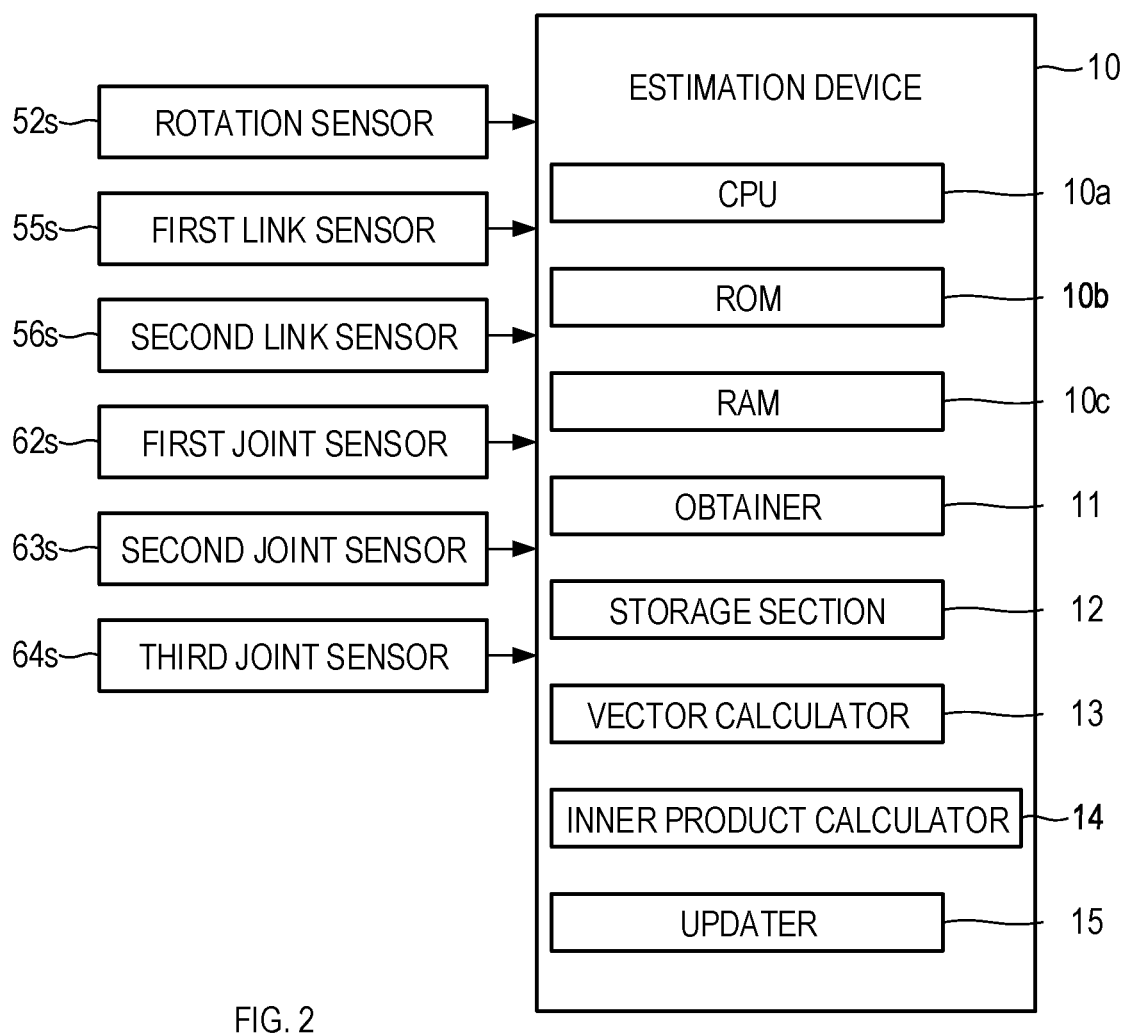
FIG. 2 is a block diagram explaining a configuration of the estimation device in FIG. 1.
Figure 3:
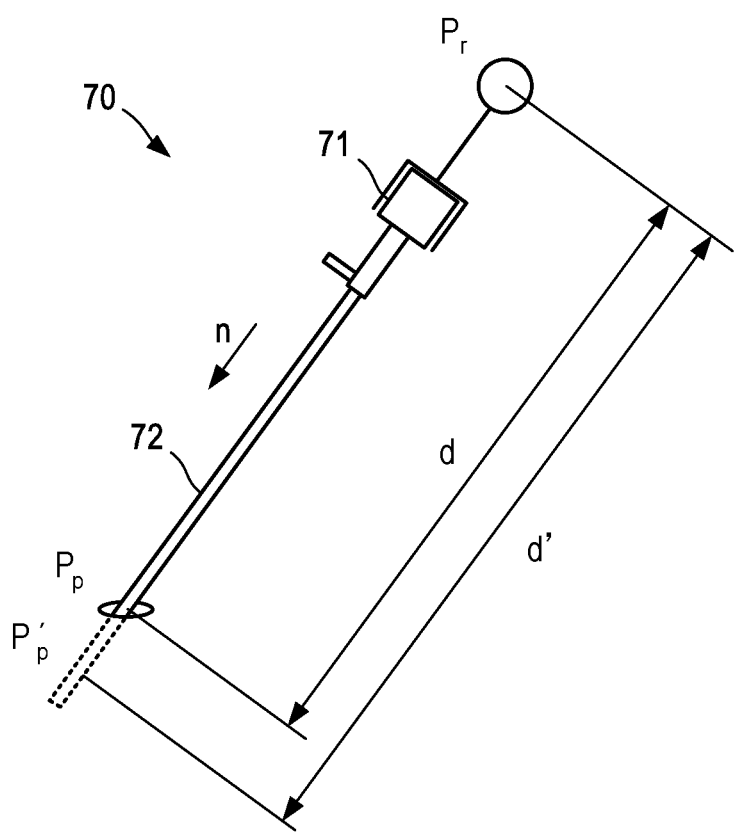
FIG. 3 is an explanatory view of a formula representing a pivot position.
Figure 4:
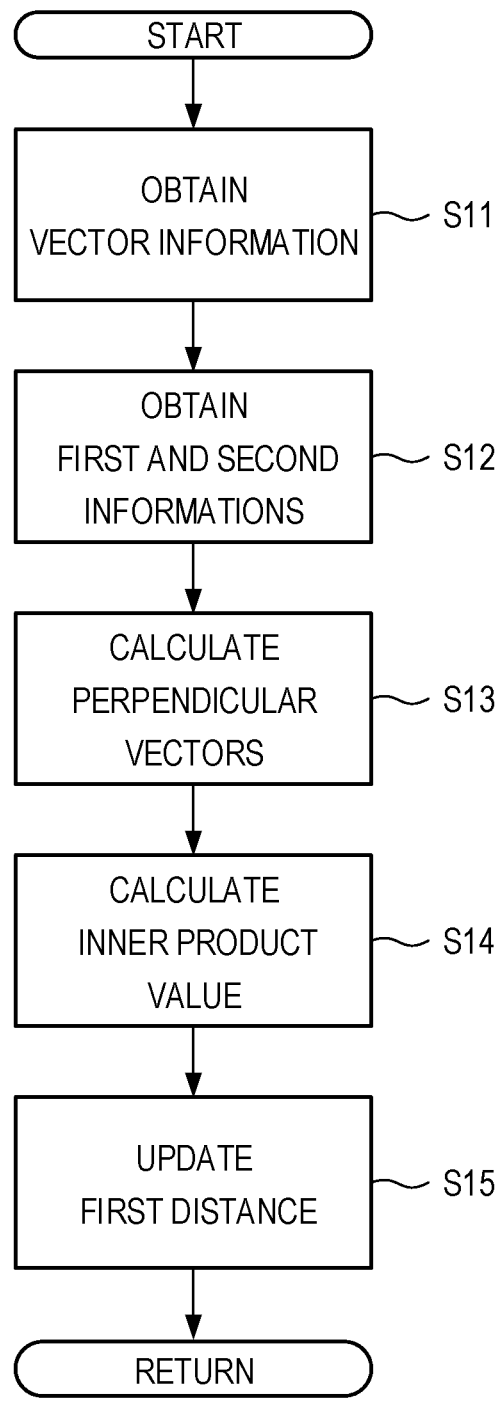
FIG. 4 is a flowchart of a calculation processing for estimating the pivot position.

The estimation device 10 is, as shown in FIGS. 1 and 2, an information processing device, such as a computer comprising a central processing unit (CPU) 10a, a ROM 10b, a RAM 10c, an input/output interface, and so forth. The CPU 10a executes a program stored in the ROM 10b or a program loaded into the RAM 10c. Upon execution of the program, functions as at least an obtainer 11, a storage section 12, a vector calculator 13, an inner product calculator 14, and an updater 15 are exerted. Further, in response to the execution of the program, a method corresponding to the program is performed. In this example, the ROM 10b or the RAM 10c corresponds to a non-transitory tangible storage medium storing the program. It is to be noted that the estimation device 10 may comprise an electronic circuit not having a CPU (for example, an integrated circuit such as an ASIC), and all or part of the functions of the estimation device 10 may be performed using the electronic circuit.

The obtainer 11 acquires the rotation angles output from the rotation sensor 52s, the first link sensor 55s, the second link sensor 56s, the first joint sensor 62s, the second joint sensor 63s, and the third joint sensor 64s.

The obtainer 11 calculates vector information, which is information on a vector n representing an orientation of the holder 65 of the arm device 50 or an orientation of the surgical tool 70, on the basis of the obtained rotation angles. Further, the obtainer 11 also calculates information on a first movement vector $\Delta P_p'$ (hereinafter, first information), and information on a second movement vector $\Delta P_r$ (hereinafter, second information) in a similar manner. The first movement vector $\Delta P_p'$ represents a movement of a provisional pivot position (i.e., a first position) $P_p'$ of the surgical tool 70, which will be described below. In other words, the first movement vector $\Delta P_p'$ represents a movement of a part of the surgical tool 70 where the first position is located. The second movement vector $\Delta P_r$ represents a movement of a rear end portion (i.e., a second position) $P_r$, which is an end of the surgical tool 70 on the holder 65 side. In other words, the second movement vector $\Delta P_r$ represents a movement of a part of the surgical tool 70 where the second position is located.

In the present embodiment, as one example, the second movement vector $\Delta P_r$ represents the movement of the rear end portion $P_r$ of the surgical tool 70. However, not limited to this, the second position may be a position other than the rear end portion and different from the provisional pivot position $P_p'$, in the surgical tool 70, and the second movement vector $\Delta P_r$ may represent a movement of this second position.

The storage section 12 is configured as, for example, the RAM 10c, and stores a value of a first distance d' determined in advance. For purpose of estimation of the pivot position $P_p$ relative to the arm device 50, the first distance d' is used together with the front end position of the arm device 50 and the vector n representing the orientation of the surgical tool 70.

Specifically, the first distance d' represents a distance from the font end position of the arm device 50 to the provisional pivot position $P_p'$. In the present embodiment, as one example, the front end position of the arm device 50 is a reference point on the rear end side of the surgical tool 70 held by the arm device 50, or more particularly, the rear end portion $P_r$ of the main body 71. That is, a length from the rear end portion $P_r$ of the surgical tool 70 to the provisional pivot position $P_p'$ is the first distance d'.

Here, the provisional pivot position $P_p'$ is a position determined in advance, and is used when the actual pivot position $P_p$ is estimated. Thus, the actual pivot position $P_p$ and the provisional pivot position $P_p'$ may be identical to or different from each other. It is preferable that the provisional pivot position $P_p'$ is set on the surgical tool 70, but may be set outside the surgical tool 70.

When the first distance d' is calculated, instead of the front end position of the arm device 50, a reference point on the front end side of the surgical tool 70, or more particularly, for example, a front end portion of the surgical tool 70 may be used. In this case, the first distance d' is a length from the front end portion of the surgical tool 70 to the provisional pivot position $P_r'$.

The vector calculator 13 calculates a direction of an axis L of the surgical tool 70, as well as a first perpendicular vector $\Delta P_p\bot'$ and a second perpendicular vector $\Delta P_r\bot$. Here, the direction of the axis L of the surgical tool 70 is calculated on the basis of the vector information. The first perpendicular vector $\Delta P_p\bot'$ and the second perpendicular vector $\Delta P_r\bot$ are components of the first movement vector $\Delta P_p'$ and the second movement vector $\Delta P_r$, respectively, and the components are perpendicular to the direction of the axis L.

The inner product calculator 14 calculates an inner product of the first perpendicular vector $\Delta P_p\bot'$ and the second perpendicular vector $\Delta P_r\bot$.

The updater 15 calculates a new first distance d' by adding a value of the inner product multiplied by a specified coefficient k to the first distance d' stored in the storage section 12. Further, the updater 15 updates a value of the first distance d' stored in the storage section 12 to a value of the new first distance d' obtained by this calculation.

Next, a calculation processing for estimating the pivot position $P_p$ by the estimation device 10 will be described. Firstly, a formula expressing the pivot position $P_p$ is explained with reference to FIG. 3. The pivot position $P_p$ is expressed by the following formula (1), using the rear end portion $P_r$ (the front end position of the arm device 50), the vector n, and a distance d.

[Formula 1]

Next, the calculation processing for estimating the pivot position $P_p$ is explained. Upon starting the calculation processing for estimating the pivot position $P_p$ shown in FIG. 4, the estimation device 10 performs the calculation processing repeatedly based on a sampling interval determined in advance. The calculation processing is continued at least until an operation of the arm device 50 is complete.

In the calculation processing, firstly, the obtainer 11 obtains the vector information on the vector n representing the orientation of the holder 65 of the arm device 50 holding the surgical tool 70 or the orientation of the surgical tool 70 (S11). Specifically, the obtainer 11 acquires the rotation angles output from the rotation sensor 52s, the first and second link sensors 55s and 56s, and the first to third joint sensors 62s to 64s (hereinafter, also described as "the rotation sensor 52s and other sensors"). Then, the obtainer 11 calculates the vector information on the vector n on the basis of the obtained rotation angles.

Next, the obtainer 11 obtains the above-described first information on the first movement vector $\Delta P_p'$ and the above-described second information on the second movement vector $\Delta P_r$ (S12). Specifically, the obtainer 11 calculates the first and second informations on the basis of the most recently obtained rotation angles output from the rotation sensor 52s and other sensors, and on the basis of the previously obtained rotation angles (for example, at any of the sampling intervals prior to the most recent sampling interval), output from the rotation sensor 52s and other sensors.

Then, the vector calculator 13 calculates the first perpendicular vector $\Delta P_p\bot'$ and the second perpendicular vector $\Delta P_r\bot$ (S13). Specifically, the vector calculator 13 firstly calculates the direction of the axis L of the surgical tool 70 on the basis of the vector information on the vector n. Subsequently, the vector calculator 13 calculates the first perpendicular vector $\Delta P_p\bot'$ and the second perpendicular vector $\Delta P_r\bot$, on the basis of the first and second informations and the direction of the axis L of the surgical tool 70 (see FIG. 4).

After the first perpendicular vector $\Delta P_p\bot'$ and the second perpendicular vector $\Delta P_r\bot$ are calculated, the inner product calculator 14 calculates an inner product value $\Delta d'$ of the first perpendicular vector $\Delta P_p\bot'$ and the second perpendicular vector $\Delta P_r\bot$ (S14).

Figure 5:
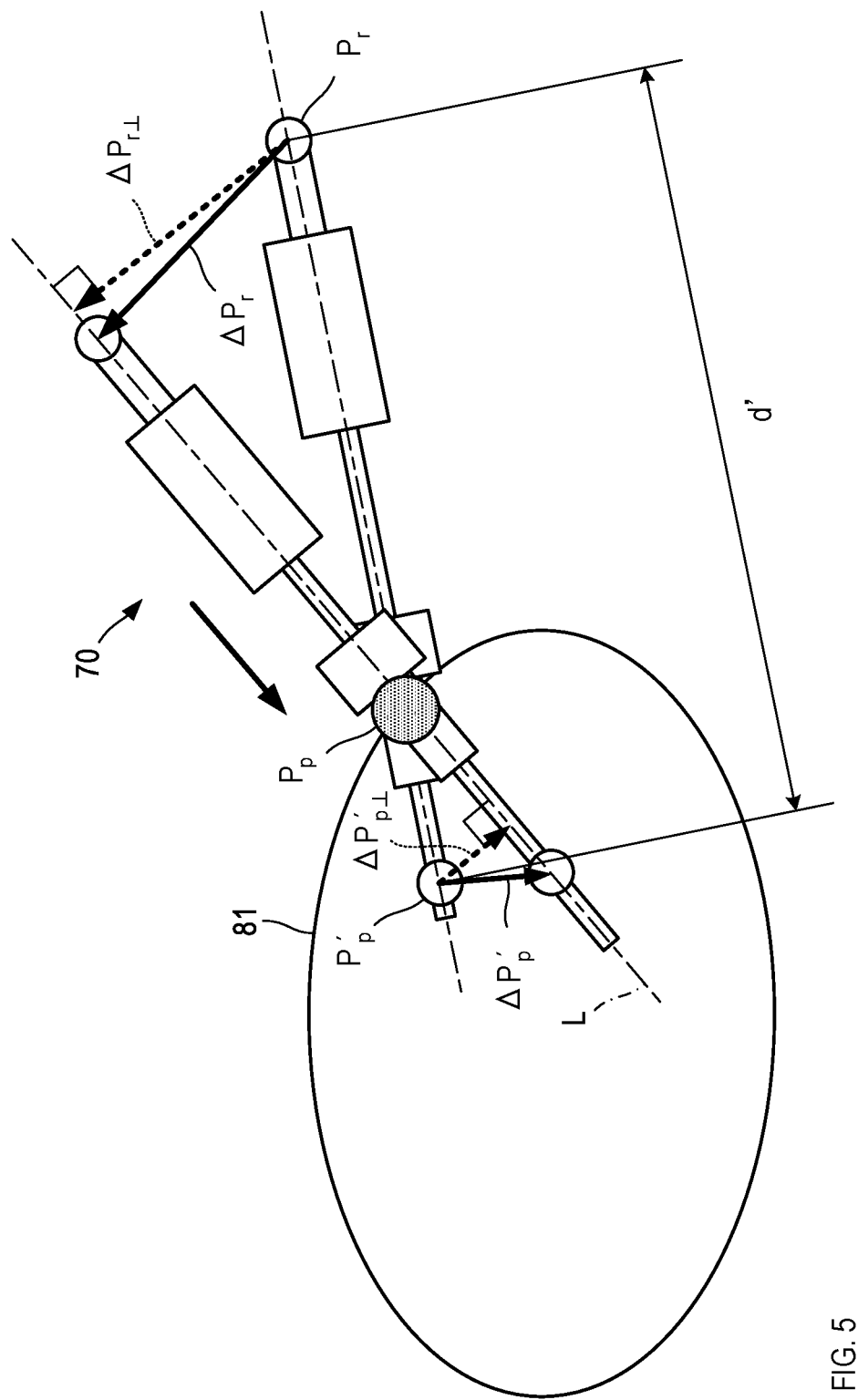
FIG. 5 is an explanatory diagram of the calculation processing for estimating the pivot position.

For example, as shown in FIG. 5, if the first distance d' is greater than a second distance d from the front end position of the arm device 50 to the pivot position $P_p$, the provisional pivot position $P_p'$ is located closer to a front end of the surgical tool 70 than the pivot position $P_p$. In this case, a direction of the first perpendicular vector $\Delta P_p\bot'$ is opposite to a direction of the second perpendicular vector $\Delta P_r\bot$. Accordingly, the inner product value $\Delta d'$ of the first and second perpendicular vectors is negative.

Figure 6:
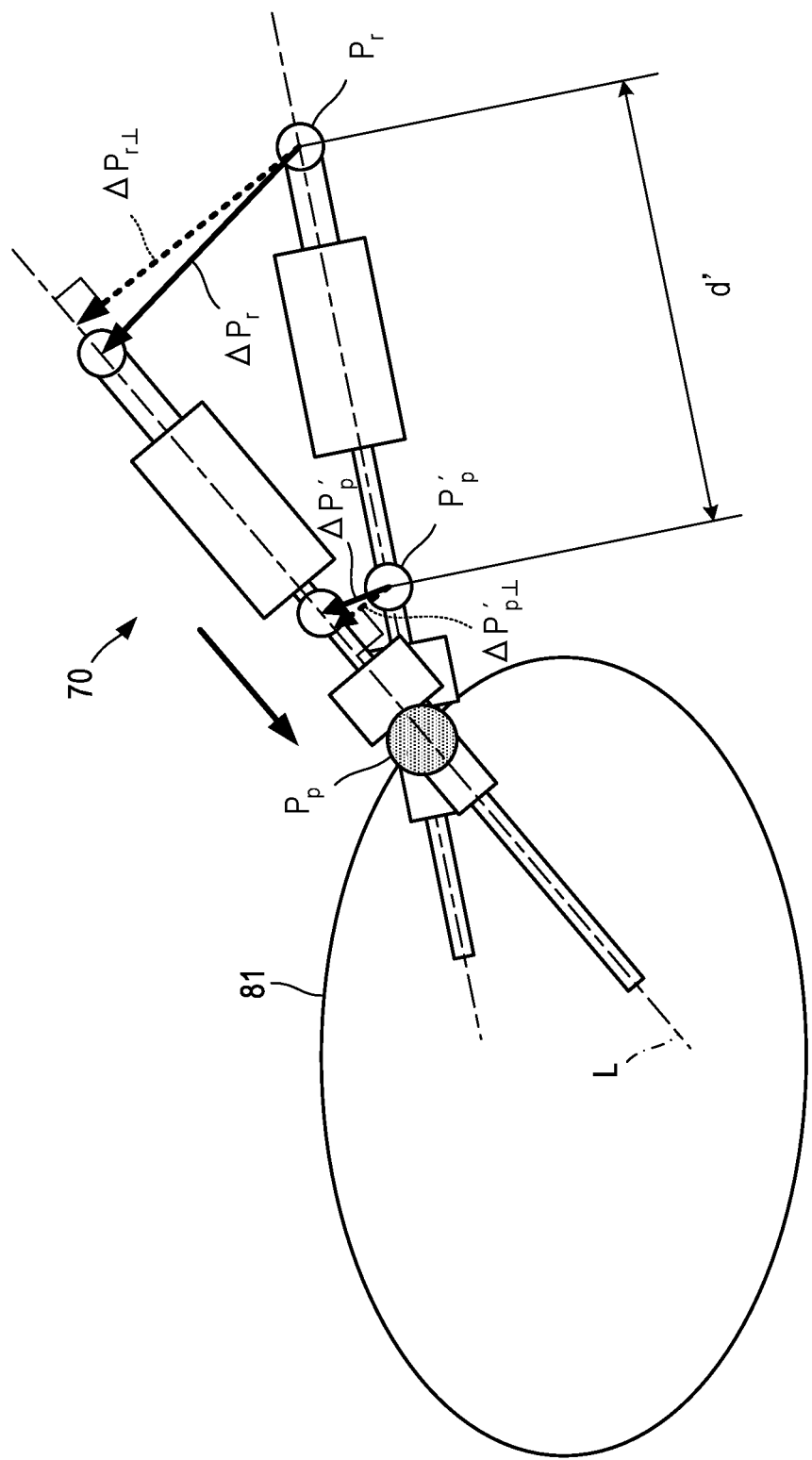
FIG. 6 is an explanatory diagram of the calculation processing for estimating the pivot position.

On the other hand, as shown in FIG. 6, if the first distance d' is smaller than the second distance d, the provisional pivot position $P_p'$ is located closer to the rear end portion $P_r$ than the pivot position $P_p$. In this case, the direction of the first perpendicular vector $\Delta P_p\bot'$ is the same as that of the second perpendicular vector $\Delta P_r\bot$. Accordingly, the inner product value $\Delta d'$ of the first and second perpendicular vectors is positive.

After the inner product value $\Delta d'$ is calculated, the updater 15 modifies and updates the first distance d' (S15). Specifically, the updater 15 adds the inner product value $\Delta d'$ multiplied by the specified coefficient k (where k is a positive value) to the first distance d' stored in the storage section 12. Further, the updater 15 updates the stored value of the first distance d' to the value obtained by the above mentioned addition.

For example, in the case shown in FIG. 5, the first distance d' is made smaller by the aforementioned update, thus approaching the second distance d. On the other hand, in the case shown in FIG. 6, the first distance d' is made greater by the aforementioned update, thus approaching the second distance d.

The aforementioned coefficient k may be set to a desired value. For example, if the coefficient k is greater, the first distance d' can be made closer to the second distance d more quickly. However, it may become difficult for the first distance d' to converge to the second distance d. Further, if the coefficient k is smaller, the first distance d' slowly approaches the second distance d, and it becomes easier for the first distance d' to converge to the second distance d.

Figure 7:
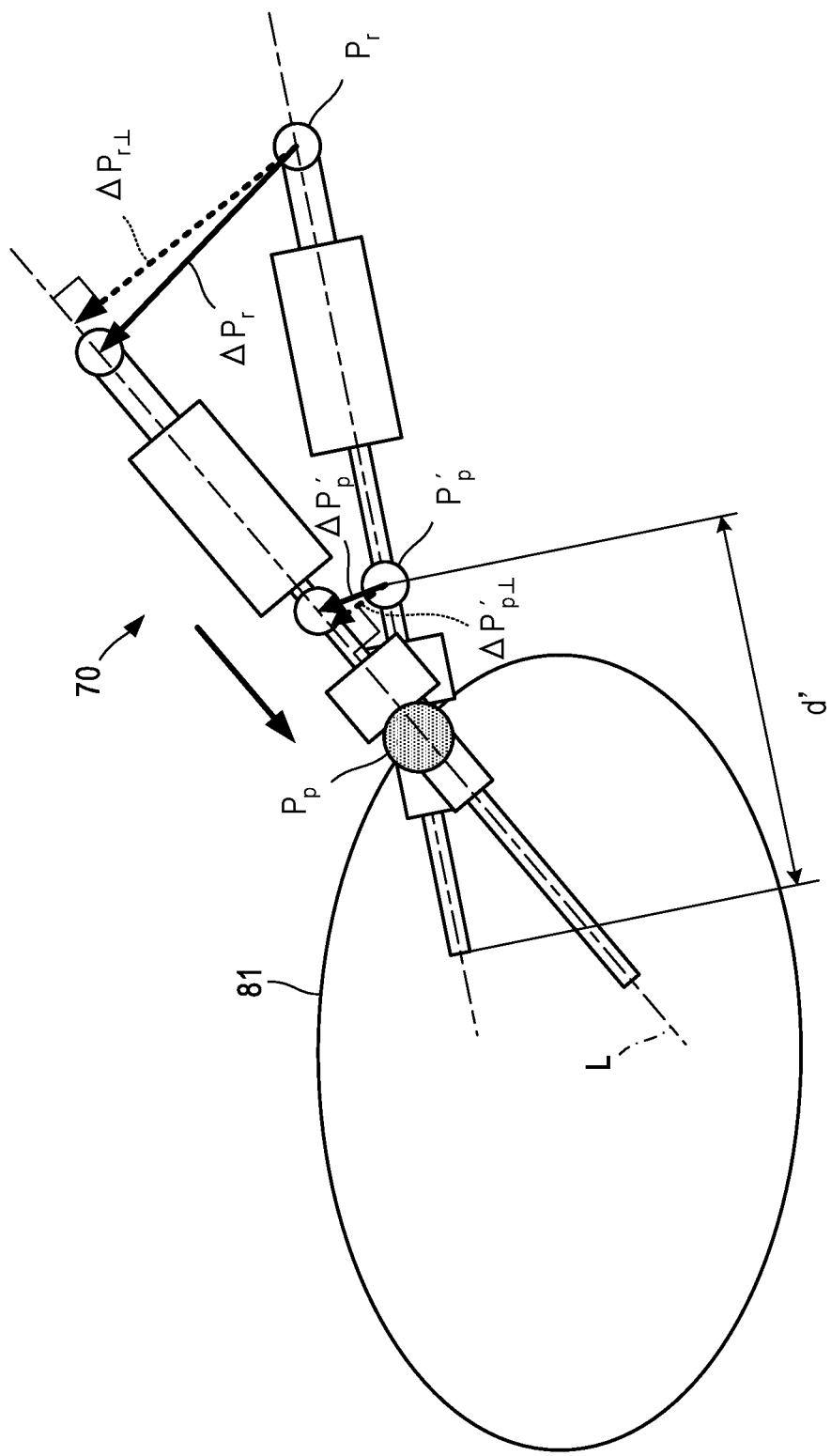
FIG. 7 is an explanatory diagram of the calculation processing for estimating the pivot position.

It is to be noted that, if the first distance d' represents a distance from the front end portion of the surgical tool 70 to the provisional pivot position $P_p'$ as shown in FIG. 7, the inner product value Δd' used for updating the first distance d' in S15 is reversed in positive and negative. If the first distance d' is greater than the second distance d, the inner product value Δd' is positive. If the first distance d' is smaller than the second distance d, the inner product value Δd' is negative. Thus, it is preferable that the coefficient k is a negative value.

The estimation device 10 mentioned above enables the following things, The first perpendicular vector $\Delta P_p \perp'$ at the provisional pivot position (first position) $P_p'$ and the second perpendicular vector $\Delta P_r \perp$ at the second position different from the provisional pivot position $P_p'$ are calculated, and the first distance d' is updated on the basis of the inner product of the first and second perpendicular vectors. This enables estimation of the pivot position $P_p$ of the surgical tool 70.

The rear end portion $P_r$ of the surgical tool 70 is determined as the second position. This makes it easier to estimate the pivot position $P_p$ of the surgical tool 70.

The rotation angles of the joints of the arm device 50 measured by the rotation sensor 52s and other sensors are used as the vector information. This makes it easier to obtain the vector information.

The rotation angles measured by the rotation sensor 52s and other sensors at least after a specified time interval are used as the first information on the first movement vector $\Delta P_p'$ and as the second information on the second movement vector $\Delta P_r$. This makes it easier to obtain the first information and the second information.

The first distance d' is repeatedly updated at the specified sampling intervals. This allows an increase in estimation accuracy of the pivot position $P_p$ of the surgical tool 70. Also, if the pivot position $P_p$ of the surgical tool 70 is moved due to some cause and the estimation accuracy is impaired, the first distance d' is repeatedly updated at the sampling intervals, thereby allowing a re-increase in the estimation accuracy of the pivot position $P_p$.

It is to be noted that a technical scope of the present disclosure is not limited to the aforementioned embodiments, and various modifications may be added without departing from the spirit of the present disclosure. For example, in the above-described embodiments, the estimation device 10 is described using an example where the estimation device 10 is disposed separately from the arm device 50 and its controller, but the estimation device 10 may be configured so as to be built in the arm device 50 and its controller.

Further, the present disclosure may be implemented in various forms including not only the above-described estimation device 10, but also a system including the estimation device 10 as a constituent element, a program for allowing a computer to function as the estimation device 10, a non-transitory tangible storage medium, such as a semiconductor memory, storing this program, or a method corresponding to the processing executed by the estimation device 10.

The invention claimed is:

1. An estimation device configured to estimate a pivot position of a surgical tool, a rear end side of which being held by a holder of an arm, the arm including at least one joint, the estimation device comprising:
   a storage section configured to store a first distance, the first distance being:
      a length from a reference point on the rear end side of the surgical tool to a first position, which is a provisional pivot position, or
      a length from a reference point on a front end side of the surgical tool to the first position, the front end side being opposite to the rear end side;
   an obtainer configured to obtain:
      vector information, which is information on an orientation of the holder of the arm or on an orientation of the surgical tool,
      first information on a movement of the first position of the surgical tool, and
      second information on a movement of a second position of the surgical tool, the second position being different from the first position;
   a vector calculator configured to calculate a direction of an axis of the surgical tool based on the vector information, and to individually calculate, based on the first information, the second information, and the direction of the axis of the surgical tool, a first perpendicular vector, which is a component of a vector in the movement of the first position, the component being perpendicular to the direction of the axis, and a second perpendicular vector, which is a component of a vector in the movement of the second position, the component being perpendicular to the direction of the axis;
   an inner product calculator configured to calculate an inner product of the first perpendicular vector and the second perpendicular vector; and
   an updater configured to update the first distance by adding a value of the inner product multiplied by a specified coefficient to the first distance stored in the storage section.

2. The estimation device according to claim 1, wherein the second position is located in a rear end portion of the surgical tool.

3. The estimation device according to claim 1, wherein the vector information comprises a rotation angle of the at least one joint measured by an angle sensor, and
wherein the vector calculator calculates the direction of the axis of the surgical tool based on the rotation angle obtained from the angle sensor.

4. The estimation device according to claim 1, wherein the first information and the second information comprise a rotation angle of the at least one joint measured after a specified time interval, and
wherein the vector calculator calculates the first perpendicular vector and the second perpendicular vector based on the rotation angle of the at least one joint measured after the specified time interval.

5. The estimation device according to claim 1,
wherein the obtainer obtains the vector information, the first information, and the second information at specified sampling intervals,
wherein the vector calculator calculates the first perpendicular vector and the second perpendicular vector at the specified sampling intervals,
wherein the inner product calculator calculates the inner product at the specified sampling intervals, and
wherein the updater updates the first distance at the specified sampling intervals.

6. An estimation method for estimating a pivot position of a surgical tool, a rear end side of which being held by a holder of an arm, the arm including at least one joint, the estimation method comprising:
obtaining vector information, which is information on an orientation of the holder of the arm or on an orientation of the surgical tool;
obtaining first information on a movement of a first position, which is a provisional pivot position of the surgical tool, and second information on a movement of a second position of the surgical tool, the second position being different from the first position;
calculating a direction of an axis of the surgical tool based on the vector information obtained, and individually calculating, based on the first information, the second information, and the direction of the axis of the surgical tool, a first perpendicular vector, which is a component of a vector in the movement of the first position, the component being perpendicular to the direction of the axis, and a second perpendicular vector, which is a component of a vector in the movement of the second position, the component being perpendicular to the direction of the axis;
calculating an inner product of the first perpendicular vector and the second perpendicular vector; and
updating a first distance, which is a length from a reference point on the rear end side of the surgical tool to the first position, or which is a length from a reference point on a front end side of the surgical tool to the first position, the front end side being opposite to the rear end side, by adding a value of the inner product multiplied by a specified coefficient to the first distance.

7. A non-transitory computer readable medium storing a program for estimating a pivot position of a surgical tool, a rear end side of which being held by a holder of an arm, the arm including at least one joint, the program causing a computer to execute functions comprising:
obtaining vector information, which is information on an orientation of the holder of the arm or on an orientation of the surgical tool;
obtaining first information on a movement of a first position, which is a provisional pivot position of the surgical tool, and second information on a movement of a second position of the surgical tool, the second position being different from the first position;
calculating a direction of an axis of the surgical tool based on the vector information obtained, and individually calculating, based on the first information, the second information, and the direction of the axis of the surgical tool, a first perpendicular vector, which is a component of a vector in the movement of the first position, the component being perpendicular to the direction of the axis, and a second perpendicular vector, which is a component of a vector in the movement of the second position, the component being perpendicular to the direction of the axis;
calculating an inner product of the first perpendicular vector and the second perpendicular vector; and
updating a first distance, which is a length from a reference point on the rear end side of the surgical tool to the first position, or which is a length from a reference point on a front end side of the surgical tool to the first position, the front end side being opposite to the rear end side, by adding a value of the inner product multiplied by a specified coefficient to the first distance.

\* \* \* \* \*